US00PP26336P2

(12) United States Plant Patent
Bean

(10) Patent No.: US PP26,336 P2
(45) Date of Patent: Jan. 19, 2016

(54) ***AGAPANTHUS* PLANT NAMED 'ANDBIN'**

(50) Latin Name: ***Agapanthus* hybrid**
Varietal Denomination: ANDBIN

(71) Applicant: Charles Andrew de Wet, Johannesburg (ZA)

(72) Inventor: Quinton Bean, Johannesburg (ZA)

(73) Assignee: Charles Andrew De Wet, Johannesburg (ZA)

( * ) Notice: Subject to any disclaimer, the term of this patent is extended or adjusted under 35 U.S.C. 154(b) by 109 days.

(21) Appl. No.: 14/120,128

(22) Filed: Apr. 28, 2014

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Susan McCormick Ewoldt
(74) *Attorney, Agent, or Firm* — Penny J. Aguirre

(57) ABSTRACT

A new cultivar of *Agapanthus*, 'ANDBIN', that is characterized by its fast growing and fast multiplying growth habit, its compact plant habit, it inflorescences that form dense umbels of flowers that are dark blue-violet in color, its extended flowering season blooming and re-blooming from July to January in South Africa, its very floriferous blooming period producing an unusually high number of inflorescences, and its good resistance to fungal infection from *Macrophoma agapanthii*.

2 Drawing Sheets

Botanical classification: *Agapanthus* hybrid.
Varietal denomination: 'ANDBIN'.

BACKGROUND OF THE INVENTION

The present invention relates to a new and distinct cultivar of *Agapanthus* of hybrid origin and will be referred to hereafter by its cultivar name, 'ANDBIN'. 'ANDBIN' represents a new perennial herb grown for landscape use.

The new cultivar was derived from a controlled breeding program by the Inventor in Hartebeespoort, Northwest Province, South Africa. The objective of the breeding program is to develop new cultivars of *Agapanthus* that are fast growing, early flowering and that display repeat flowering and unique flower colors. The Inventor made a cross in October of 2007 between an unnamed plant of *Agapanthus caulescens* hybrid from the Inventor's breeding program as the female parent and an unnamed plant of *Agapanthus campanulatus* hybrid from the Inventor's breeding program as the male parent. The Inventor selected 'ANDBIN' in November of 2009 as a single unique plant amongst the seedlings that resulted from the above cross.

Asexual propagation of the new cultivar was first accomplished by division by the Inventor in Hartebeespoort, Northwest Province, South Africa in February of 2010. Asexual propagation by division and tissue culture has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'ANDBIN' as a distinct cultivar of *Agapanthus*.

1. 'ANDBIN' exhibits a fast growing and fast multiplying growth habit.
2. 'ANDBIN' exhibits a compact plant habit.

3. 'ANDBIN' exhibits inflorescences that form dense umbels of flowers that are dark blue-violet in color.
4. 'ANDBIN' exhibits an extended flowering season blooming and re-blooming from July to January in South Africa.
5. 'ANDBIN' exhibits a very floriferous blooming period producing an unusually high number of inflorescences.
6. 'ANDBIN' exhibits good resistance to fungal infection from *Macrophoma agapanthii*.

The female parent of 'ANDBIN' differs from 'ANDBIN' in having a shorter flowering season, in having few flowers per inflorescence, and in producing fewer inflorescences. The male parent of 'ANDBIN' differs from 'ANDBIN' in being slower growing, in having a shorter flowering season, in being more susceptible to disease, and in having flowers that are darker in color. 'ANDBIN' can be most closely compared to the *Agapanthus* cultivars 'Benfran' (U.S. Plant Pat. No. 21,705) and 'ATIBlu' (U.S. Plant Pat. No. 14,332). 'Benfran' is similar to 'ANDBIN' in having a compact plant habit and in being fast to multiply. 'Benfran' differs from 'ANDBIN' in being less cold tolerant, in having flowers that are lighter blue in color, in having fewer inflorescences, and in exhibiting very little to no re-blooming. 'ATIBlu' is similar to 'ANDBIN' in being a prolific producer of inflorescences and in exhibiting good cold tolerant. 'ATIBlu' differs from 'ANDBIN' in having flowers that are pale blue in color, in having a shorter flowering season, in exhibiting less re-blooming, in having flowering stems that are taller in height, and in having leaves that are narrower.

BRIEF DESCRIPTION OF THE DRAWINGS

The accompanying colored photographs illustrate the overall appearance and distinct characteristics of the new *Agapanthus*. The photographs were taken of 14 month-old plants (from a bare root division) of 'ANDBIN' as grown outdoors in a 3-gallon container in Loxley, Ala.

The photograph in FIG. 1 provides a side view of a plant of 'ANDBIN' in bloom.

Figure 1:
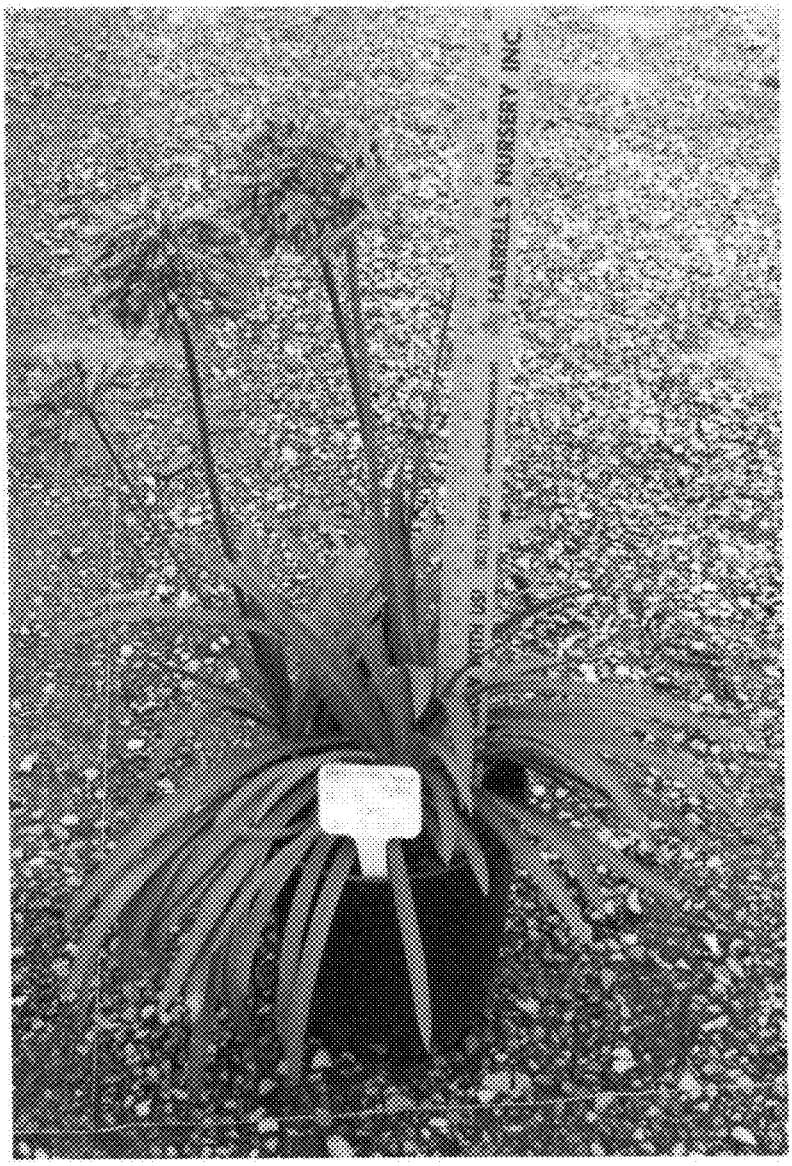
Figure 2:
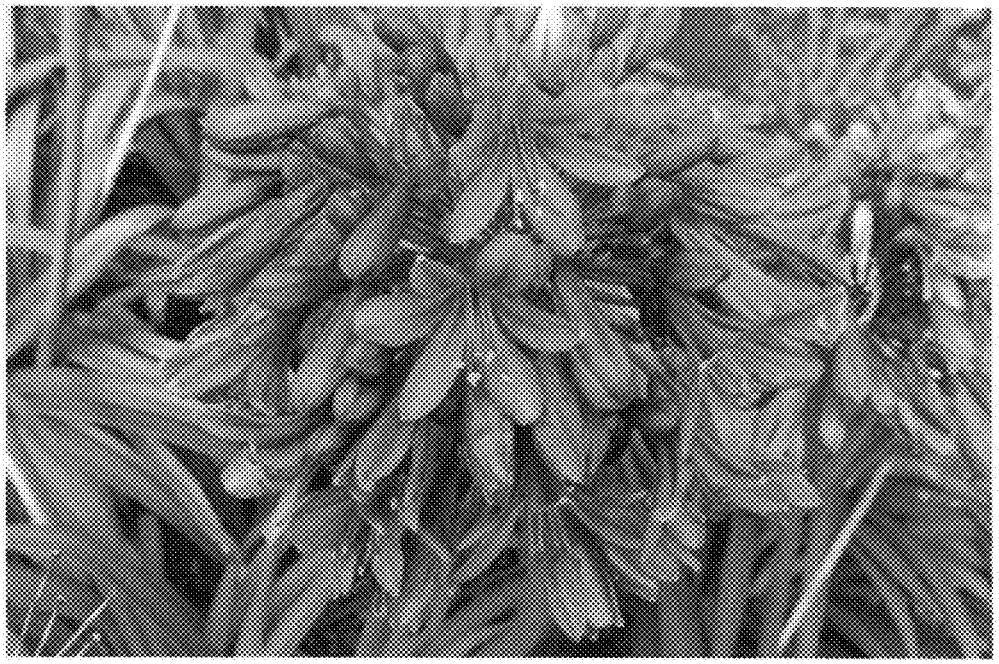

The photograph in FIG. 2 provides a close-up view of an inflorescence of 'ANDBIN'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 14 month-old plants (from a bare root division) of 'ANDBIN' as grown outdoors in 3-gallon containers in Loxley, Ala. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—Blooms and re-blooms from July to January with peak bloom in November in South Africa.

*Plant type.*—Semi-deciduous (climate dependent) herbaceous perennial.

*Plant habit.*—Basal rosettes with inflorescences emerging from the rosette center.

*Height and spread.*—Average of 60 cm in height (including inflorescences) and 35 cm in spread.

*Cold hardiness.*—At least to U.S.D.A. Zone 8.

*Diseases and pests.*—Good resistance to fungal infections by *Macrophoma agapanthii* fungus has been observed.

*Root description.*—Thick and fleshy.

*Propagation.*—Tissue culture (preferred) and division.

*Growth rate.*—Vigorous.

Foliage description:

*Leaf shape.*—Ligulate.

*Leaf division.*—Simple.

*Leaf base.*—Truncate.

*Leaf arrangement.*—2-ranked.

*Leaf apex.*—Narrow acute.

*Leaf aspect.*—Emerging leaves erect, then cascade.

*Leaf venation.*—Parallel, upper surface; matches leaf coloration, and lower surface; 138B with only mid rib conspicuous.

*Leaf margins.*—Entire.

*Leaf size.*—Up to 30 cm in length and 1.9 cm in width.

*Leaf surface.*—Smooth, glabrous, and dull on upper and lower surface.

*Leaf number.*—Average of 10 leaves per rosette.

*Leaf color.*—Young leaves, upper and lower surface; 144A and blending to N137B near apex and 145D at base, mature leaves, upper and lower surface; 137A and 145D at base.

*Leaf attachment.*—Sessile to base.

Flower description:

*Inflorescence type.*—Dense umbel.

*Flower fragrance.*—None.

*Flower type.*—Rotate, campanulate, base of tepals fused.

*Flower number.*—An average of 70 flowers per umbel.

*Inflorescence size.*—Average of 12 cm in height (excluding peduncle) and 13.2 cm in diameter.

*Flower size.*—An average of 2.9 cm in depth and 3.8 cm in diameter.

*Lastingness of inflorescence.*—Average 7 days.

*Flower aspect.*—Outward.

*Peduncle.*—1 to 2 per rosette with rebloom, strong, slightly oval in shape, held at an average angle of 0° to 15° (upright=0°), average of 45 cm in length and 1.1 cm in width at distal region and 4 mm in width at proximal region, a blend of 144A and 137A in color, satiny and glabrous surface.

*Pedicels.*—Very strong, average of 2.5 cm in length and 1 mm in width, held erect to outward (0° to 180°), color 144B to 144C.

*Flower buds.*—Obelliptic in shape, average of 2.3 cm in length and 5 mm in width, a blend of 95B to 95C and 97B to 97D in color and lightly suffused with N81A, enclosed by a deciduous spathe-like bract ovate in shape, caudate apex, truncate base, an average of 3.0 cm in width and 3.8 cm in width, color outer surface; a blend of 138B, 138C and 91A, color inner surface; a blend of 157A, 91A, and N81A, outer surface glabrous and glossy, inner surface glabrous and dull.

*Tepals.*—6 (3 inner and 3 outer), rotate, obelliptic in shape, lower 45% fused, entire margins, broadly acute apex, glabrous on inner and outer surfaces, inner and outer tepals are an average of 2.2 cm in length, inner tepals are 6 mm in width, outer tepals are 4 mm in width, color; a blend of 95B to 95D and 97B to 97D and lightly suffused with N81A.

Reproductive organs:

*Gynoecium.*—1 pistil, average of 1.9 cm in length, stigma is narrow clavate in shape and 95D in color, style is 1.9 cm in length and 95C to 95D in color, ovary is oblong in shape, 7 mm in length, 2 mm in width and 145D in color.

*Androcoecium.*—6 stamens, anthers are dorsified, obcordate in shape, average of 1 mm in length, and N155A in color, filament is 2.1 cm in length and 95C to 95D in color, pollen is moderately abundant in quantity and 188A in color.

*Fruit/seed.*—Have not been observed.

It is claimed:

1. A new and distinct cultivar of *Agapanthus* plant named 'ANDBIN' as herein illustrated and described.

* * * * *